United States Patent
Milardo et al.

(10) Patent No.: US 12,054,830 B2
(45) Date of Patent: Aug. 6, 2024

(54) NON-CHROMATIC CONVERSION COATING SYSTEM AND METHOD

(71) Applicant: Astroseal Products Mfg. Corporation, Chester, CT (US)

(72) Inventors: Michael Milardo, Old Lyme, CT (US); John Sulzbach, Killingworth, CT (US)

(73) Assignee: ASTROSEAL PRODUCTS MFG CORPORATION, Chester, PA (US)

( * ) Notice: Subject to any disclaimer, the term of this patent is extended or adjusted under 35 U.S.C. 154(b) by 651 days.

(21) Appl. No.: 17/348,067

(22) Filed: Jun. 15, 2021

(65) Prior Publication Data

US 2021/0310128 A1 Oct. 7, 2021

Related U.S. Application Data

(63) Continuation of application No. 15/807,109, filed on Nov. 8, 2017, now Pat. No. 11,035,043.

(51) Int. Cl.
| | |
|---|---|
| *B32B 15/20* | (2006.01) |
| *B32B 5/12* | (2006.01) |
| *C07D 249/18* | (2006.01) |
| *C23C 22/74* | (2006.01) |

(52) U.S. Cl.
CPC ............... *C23C 22/74* (2013.01); *B32B 5/12* (2013.01); *B32B 15/20* (2013.01); *C07D 249/18* (2013.01)

(58) Field of Classification Search
CPC ........... B32B 5/12; B32B 15/20; B64D 45/02; C27D 249/18
See application file for complete search history.

(56) References Cited

U.S. PATENT DOCUMENTS

| | | | | |
|---|---|---|---|---|
| 5,773,627 | A * | 6/1998 | Anderson | C23F 11/08 548/257 |
| 2005/0228157 | A1* | 10/2005 | Peterson | C23C 22/08 526/348.5 |

OTHER PUBLICATIONS

Li, Liangliang, et al. "Transient Formation of Chromate in Trivalent Chromium Process (TCP) Caoting on AA2024 as Probed by Raman Spectroscopy", Journal of The Electrochemical Society, 159 (8) C326-C333 (2012) (Year: 2012).*

* cited by examiner

*Primary Examiner* — Lois L Zheng
(74) *Attorney, Agent, or Firm* — CANTOR COLBURN LLP; Steven M. McHugh

(57) ABSTRACT

A system and method for coating a foil mesh with a no-chrome conversion coating is provided, wherein the system includes a solution tank, wherein the solution tank defines a tank cavity for containing a conversion coating solution, wherein the conversion coating solution comprises at least one of 5% butyl benzotriazole sodium salt and 7% alodine 5200. The system further includes a reel/roller system configured to cause the foil mesh to be disposed within the conversion coating solution for a predetermine period of time.

20 Claims, 10 Drawing Sheets

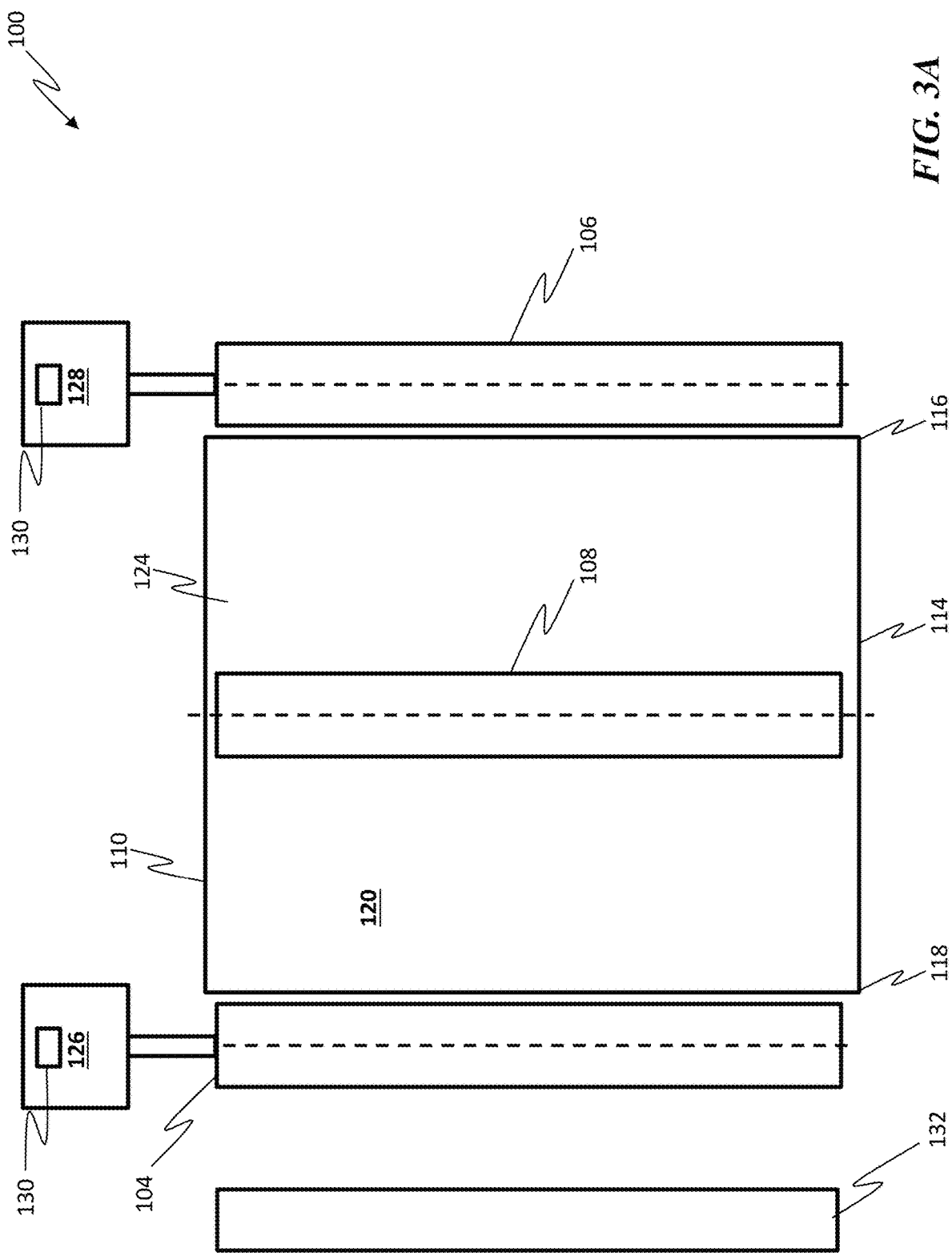

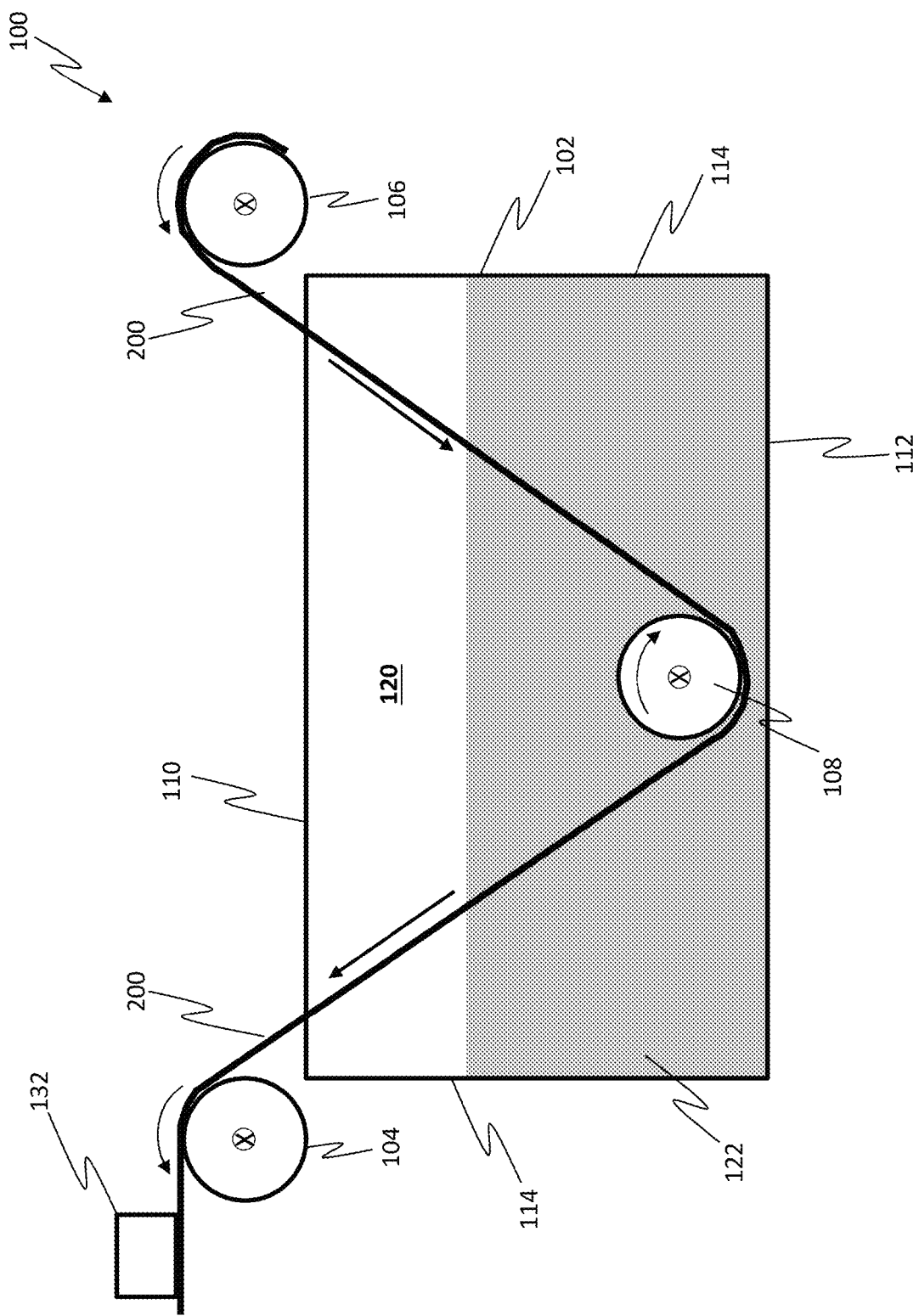

NON-CHROMATIC CONVERSION COATING SYSTEM AND METHOD

CROSS REFERENCE TO RELATED APPLICATIONS

This is a continuation application of U.S. Non-Provisional patent application Ser. No. 15/807,109 filed Nov. 8, 2017 and claims the benefit of the filing dates of U.S. Non-Provisional patent application Ser. No. 15/807,109 filed Nov. 8, 2017 and U.S. Provisional Patent Application Ser. No. 62/444,131 filed Jan. 9, 2017, the contents of both of which are incorporated herein by reference in their entireties.

FIELD OF THE INVENTION

The present invention relates generally to a method for non-chromatic conversion coating for metallic foil mesh and more particularly to a method and apparatus for non-chromatic conversion coating for aluminum and copper foil mesh.

BACKGROUND OF THE INVENTION

Lightning strikes are very common and typically may contain between 100 million and 1 billion volts of electricity with a current of up to 30,000 amperes (kA). When lightning strikes an object, it most cases it can be expected that the object will sustain a large amount of damage. This is particularly undesirable when lightning strikes an aircraft, which statistically can occur once every 1,000 to 3,000 flight hours on average. This amount of energy can have a direct impact on the structural and operational integrity of the aircraft and if the energy of the strike is allowed to impact aircraft components, the aircraft may become damaged and/or crash. For example, an aircraft typically flies farther than its own length in the time it takes a lightning strike to begin and end. This can result in multiple burn areas or other damage that could have a direct effect on a plane's structural integrity. Additionally, the indirect effects of the strike may include transient voltage strikes which can damage radio equipment, avionics and other electrically operated mechanisms, such as fuel valves. In fact, fatal accidents have occurred when current has arced around metal fasteners and ignited fuel vapors.

Accordingly, aircraft designers try to provide a continuous conductive path of low resistance over the aircraft exterior to 'direct' the energy from the lightning strike away from area's where lightning is most likely to attach, such as the radome (or nose), wingtips, nacelles and/or empennage. This 'energy redirection' is typically accomplished (at least partially) by surrounding the aircraft with a metallic material which has a relatively low resistance. Typically, an expanded foil mesh (such a aluminum, copper, etc.) which has a relatively low resistance is used to direct the energy of a lightning strike away from the composite materials and other areas of concern on an aircraft. Unfortunately, if the foil mesh is left untreated, the mesh will typically experience oxidation which may lead to corrosion and potentially fracture.

Historically, conversion coating is a chromate based solution that is applied to the expanded foil mesh to retain conductivity, inhibit corrosion and to enhance the adhesion of materials to the mesh. After the foil mesh is expanded, the mesh is treated in various baths to clean and coat the mesh in the conversion coating solution via a continuous process. Unfortunately however, chromate is a restricted chemical and the use of chromate is undesirable because of its carcinogenic characteristics and negative effects on the environment.

SUMMARY OF THE INVENTION

A system for coating a foil mesh with a no-chrome conversion coating is provided and includes a solution tank, wherein the solution tank includes a tank first end and a tank second end and defines a tank cavity for containing a conversion coating solution. The system further includes a payout reel, wherein the payout reel is located proximate the tank first end and is configured to rotate about a payout reel axis and a take-up reel, wherein the take-up reel is located proximate the tank second end and is configured to rotate about a take-up reel axis. Additionally, the system includes an idler roller, wherein the idler roller is located within the tank cavity and disposed such that when a conversion coating solution is located within the tank cavity, the idler roller is at least partially submerged within the conversion coating solution.

A system for coating a foil mesh with a no-chrome conversion coating is provided and includes a solution tank, wherein the solution tank defines a tank cavity for containing a conversion coating solution. The system further includes a payout reel, wherein the payout reel is located proximate the tank first end, a take-up reel, wherein the take-up reel is located proximate the tank second end and an idler roller, wherein the idler roller is located within the tank cavity and disposed such that when a conversion coating solution is located within the tank cavity, the idler roller is at least partially immersed within the conversion coating solution.

A method for coating a foil mesh with a non-chromate conversion coating is provided and includes expanding a foil web into a nonwoven screen, processing the nonwoven screen to remove grease and other surface contaminants, flattening the nonwoven screen to a thickness of between about 0.002 inches and about 0.006 inches to create a flattened nonwoven screen, annealing the flattened nonwoven screen to create a foil mesh, associating the foil mesh with a system for coating a foil mesh, wherein the system includes a solution tank having a tank cavity containing a conversion coating solution, bathing the foil mesh within the conversion coating solution for approximately 30 seconds to create a coated foil mesh and curing the coating foil mesh for approximately 18 hours to create an expanded foil mesh.

A system for coating a foil mesh with a no-chrome conversion coating is provided wherein the system includes a solution tank, wherein the solution tank includes a tank first end and a tank second end and defines a tank cavity for containing a conversion coating solution and wherein the conversion coating solution comprises at least one of 5% butyl benzotriazole sodium salt and 7% alodine 5200. The system further includes at least one reel configured to cause the foil mesh to traverse the solution tank and at least one roller, wherein the at least one of the at least one reel and the at least one roller is configured to immerse the foil mesh within the conversion coating solution when a conversion coating solution is located within the tank cavity.

A system for coating a foil mesh with a no-chrome conversion coating is provided, wherein the system includes a solution tank, wherein the solution tank defines a tank cavity for containing a conversion coating solution, wherein the conversion coating solution comprises at least one of 5% butyl benzotriazole sodium salt and 7% alodine 5200. The system further includes a reel/roller system configured to cause the foil mesh to be disposed within the conversion coating solution for a predetermine period of time.

A method for coating a foil mesh with a non-chromate conversion coating is provided, wherein the method includes expanding a foil web into a nonwoven screen and processing the nonwoven screen to create a foil mesh. The method further includes bathing the foil mesh within a conversion coating solution for a predetermined amount of time to create a coated foil mesh and curing the coating foil mesh for approximately 18 hours to create an expanded foil mesh.

BRIEF DESCRIPTION OF THE DRAWINGS

The foregoing and other features and advantages of the present invention should be more fully understood from the accompanying detailed description of illustrative embodiments taken in conjunction with the following Figures in which like elements are numbered alike in the several Figures:

FIG. 3A a top down view of the conversion tank of FIG. 1, having a first and second control device, in accordance with one embodiment of the invention.

FIG. 4B shows a side sectional view of a solution tank for use in conversion coating a material with a metallic web installed and being run under a vacuum, in accordance with one embodiment of the invention.

DETAILED DESCRIPTION OF THE INVENTION

Figure 1:
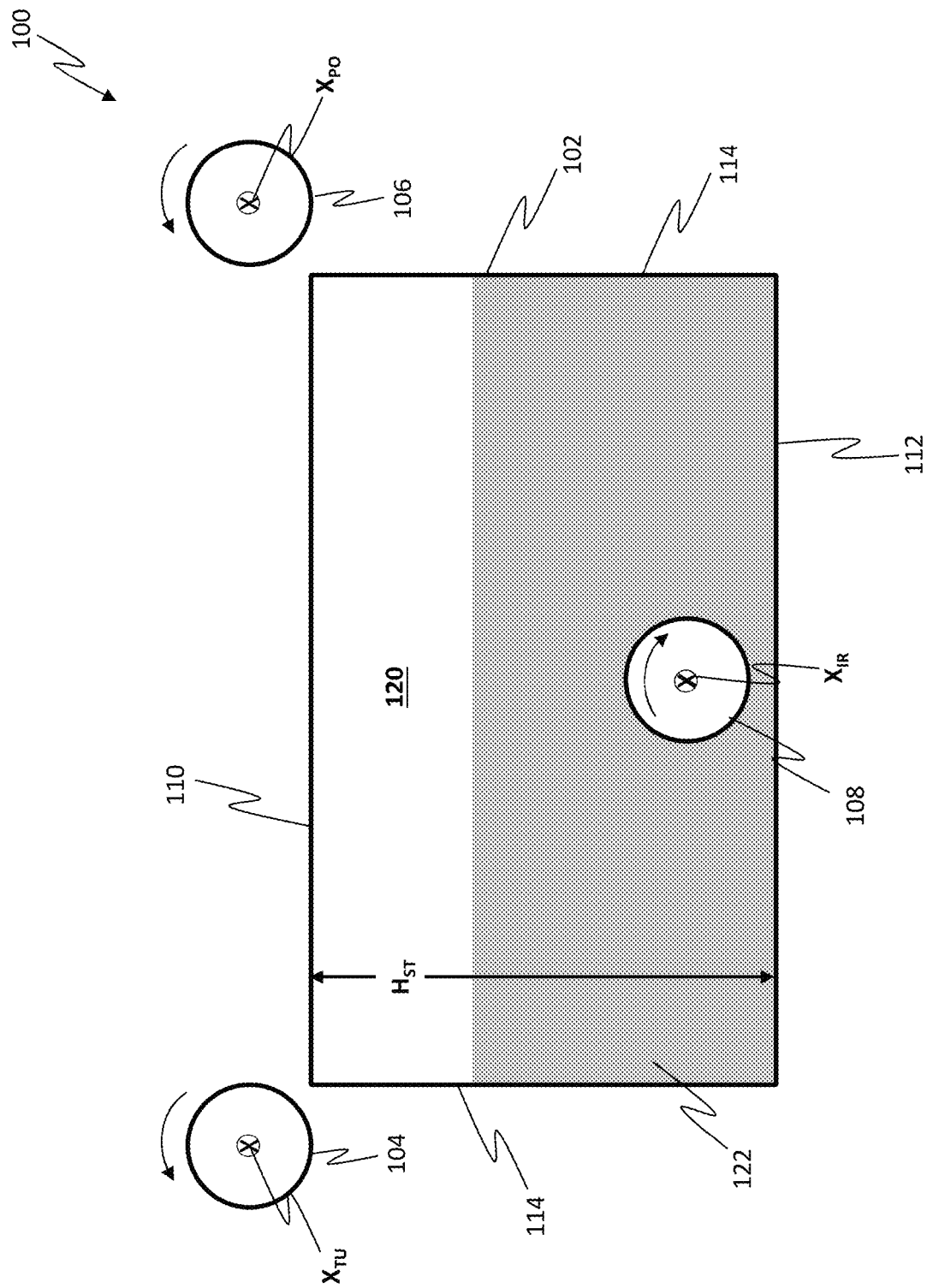
FIG. 1 shows a side sectional view of a solution tank for use in conversion coating a material, in accordance with one embodiment of the invention.
Figure 2:
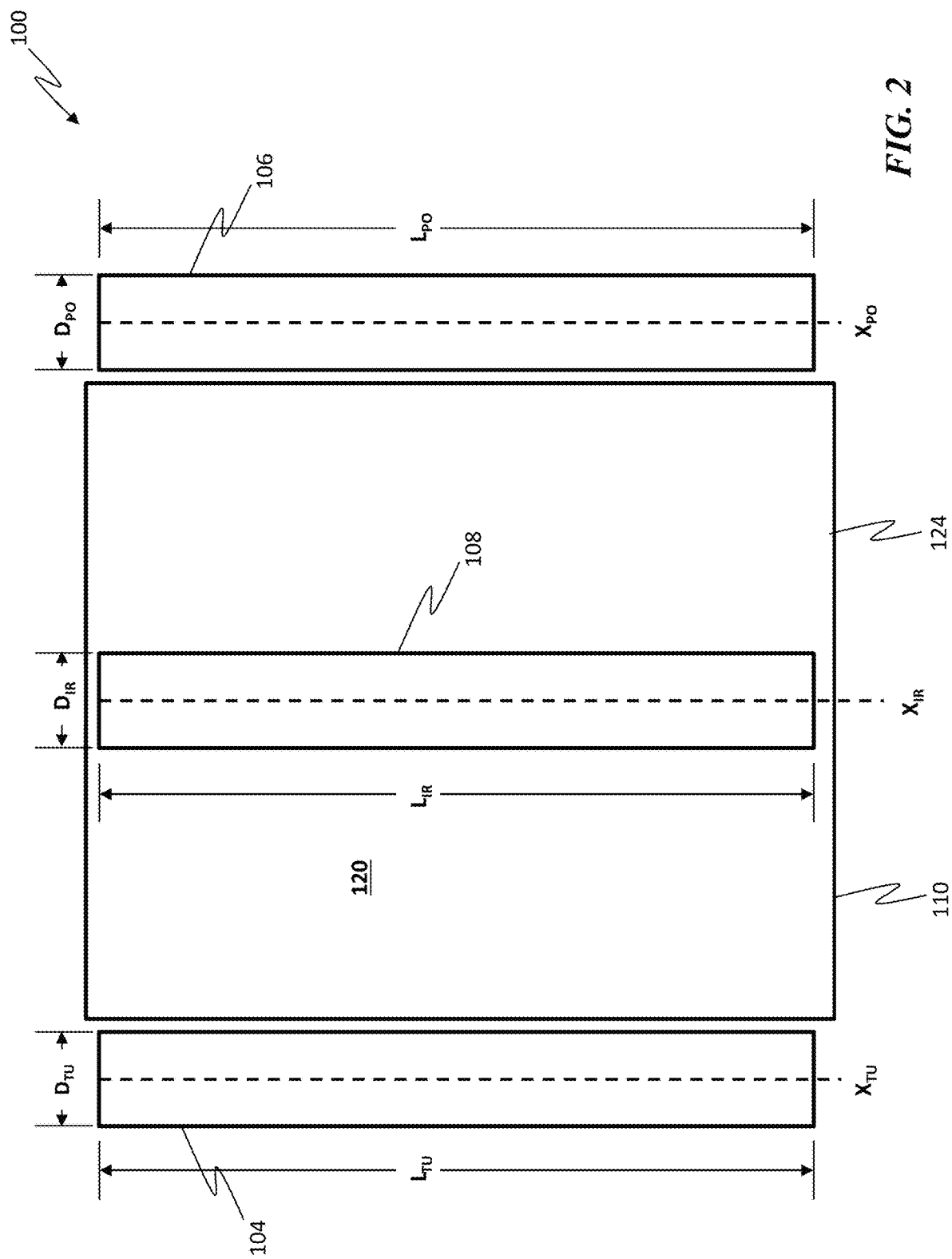
FIG. 2 shows a top down view of the conversion tank of FIG. 1.

In accordance with one embodiment of the present invention and referring to FIG. 1, FIG. 2 and FIG. 3A, a unique and novel coating system 100 for coating an aluminum and copper foil mesh with a no-chrome conversion coating is provided and includes a solution tank 102, a take-up reel 104, a payout reel 106 and an idler roller 108. The solution tank 102 includes a tank top 110, a tank bottom 112, a tank wall 114, a tank first end 116 and a tank second end 118, wherein the tank bottom 112 and the tank wall 114 define a tank cavity 120 for containing a solution 122. Additionally, the tank top 110 defines a top opening 124 which is communicated with the tank cavity 120. The take-up reel 104 is located proximate the tank first end 116, the payout reel 106 is located proximate the tank second end 118 and the idler roller 108 is located within the tank cavity 120. It should be appreciated that the tank wall 114 includes a tank wall height $H_{ST}$ which allows the tank cavity 120 to have a cavity depth of $H_{ST}$.

Figure 3B:
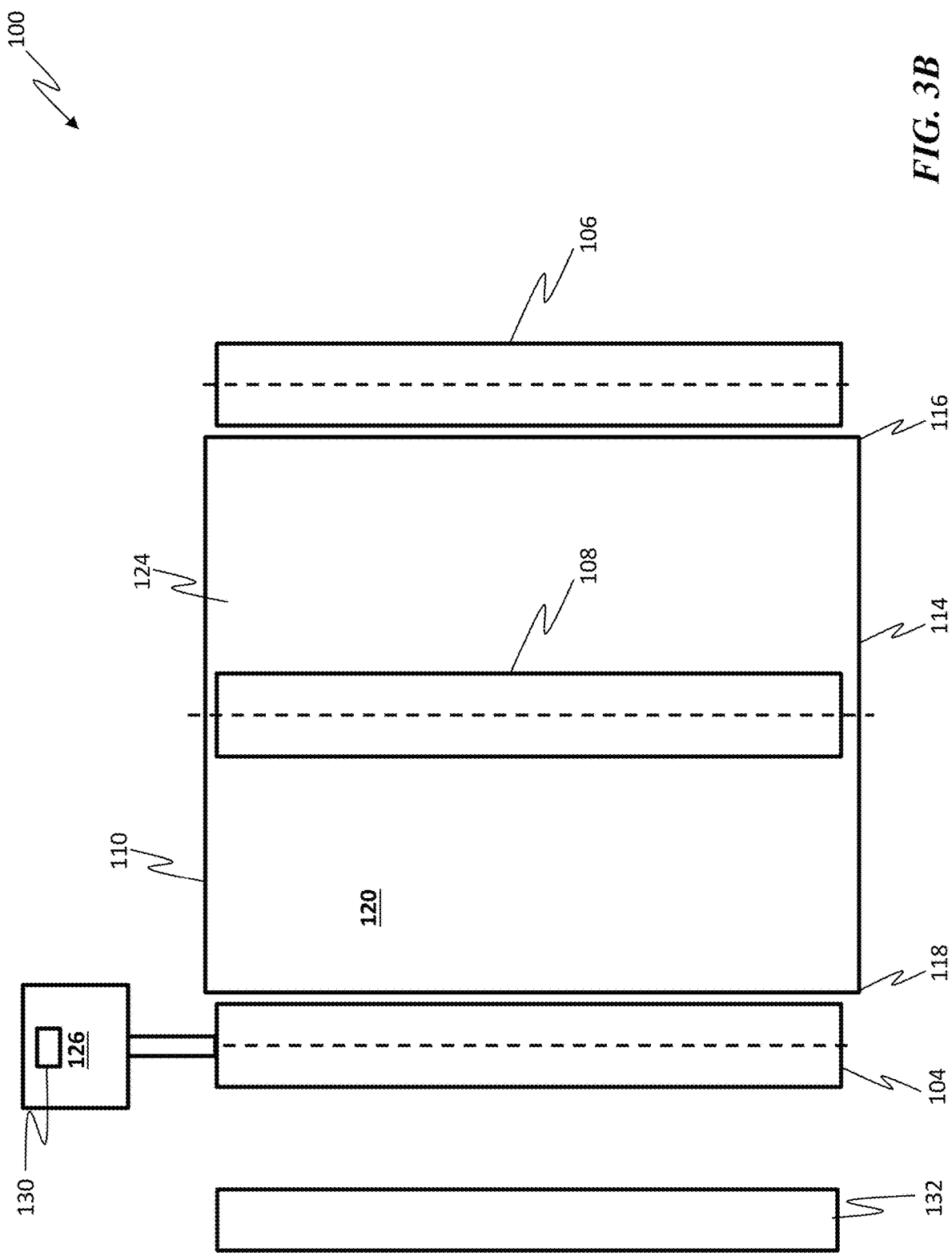
FIG. 3B a top down view of the conversion tank of FIG. 1, having only one control device, in accordance with one embodiment of the invention.

The take-up reel 104 includes a take-up reel diameter $D_{TU}$, a take-up reel length $L_{TU}$ and a take-up reel axis $X_{TU}$ which extends along the take-up reel length $L_{TU}$. The take-up reel 104 is operably associated with a first control device 126 which is configured to controllably cause the take-up reel 104 to rotate about the take-up reel axis $X_{TU}$. Additionally, the payout reel 106 includes a payout reel diameter $D_{PO}$, a payout reel length $L_{PO}$ and a payout reel axis $X_{PO}$ which extends along the payout reel length $L_{PO}$. The payout reel 106 is operably associated with a second control device 128 which is configured to controllably cause the payout reel 106 to rotate about the payout reel axis $X_{PO}$. It should be appreciated that the first control device 126 and second control device 128 may be separate control devices or may be integrated into one control device capable of separately controlling the rotation speeds of the take-up reel 104 and the payout reel 106. Additionally, the first control device 126 and/or second control device 128 may include one or more processing devices 130 that are configured to control the rotational velocity of the take-up reel 104 and/or payout reel 106. The idler roller 108 includes an idler roller diameter $D_{IR}$, an idler roller length $L_{IR}$ and an idler roller axis $X_{IR}$ which extends along the idler roller length $L_{IR}$. The idler roller 108 is configured to rotate about the idler roller axis $X_{IR}$. Referring to FIG. 3B, it should be appreciated that in one embodiment, only the take-up reel may be actively rotated and in other embodiments, only one control device 126 may be used to drive the take-up reel 104 and/or the payout reel 106.

Figure 4A:
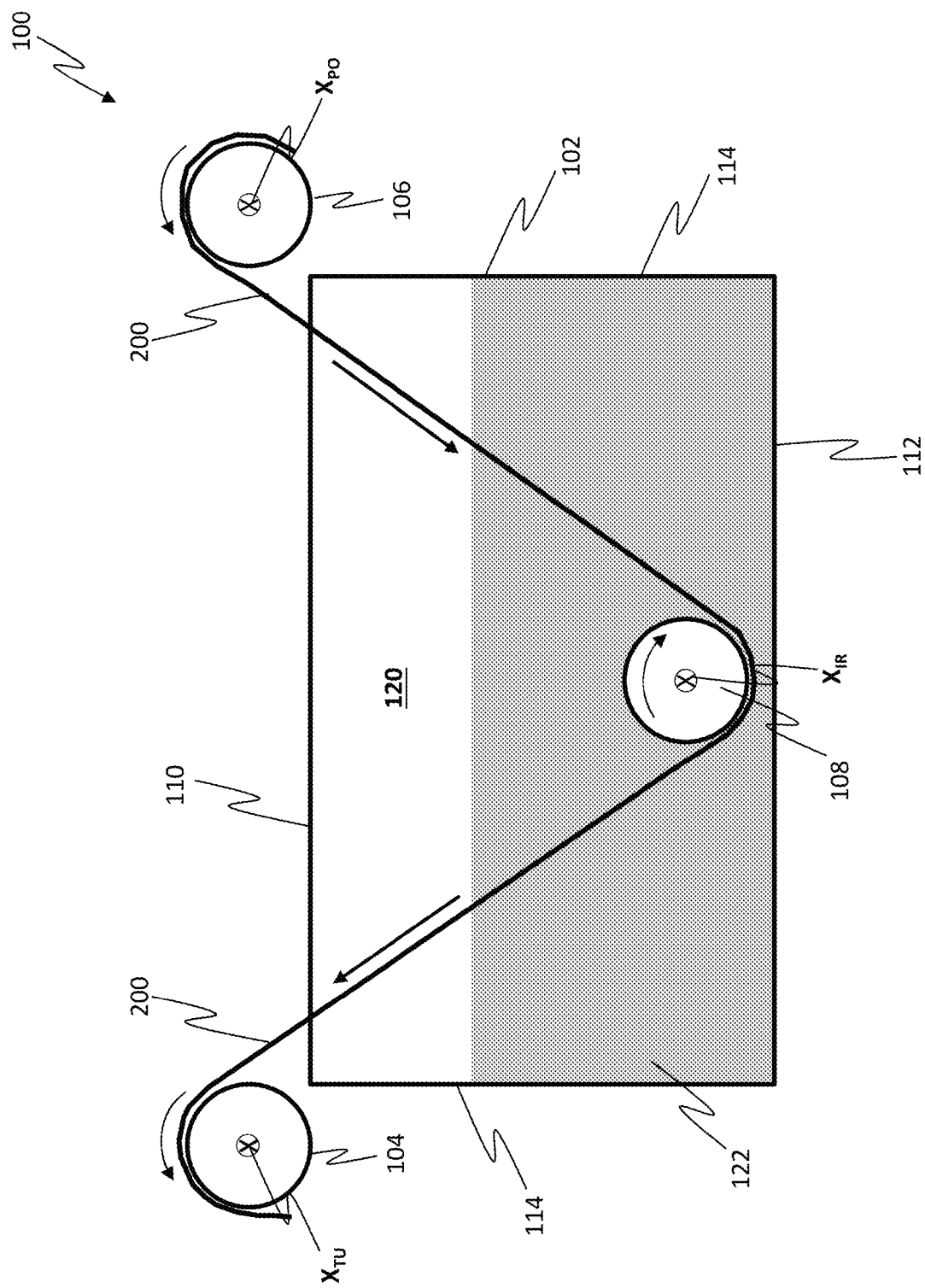
FIG. 4A shows a side sectional view of a solution tank for use in conversion coating a material with a metallic web installed, in accordance with one embodiment of the invention.

In accordance with the present invention and referring to FIG. 4A, a metallic (foil) mesh 200 (which in one embodiment may be approximately 36 inches wide and 200 linear feet long) is associated with the payout reel 106 by threading the mesh 200 over the payout reel 106 such that the mesh 200 coils around the payout reel 106 and into the tank cavity 120. The mesh 200 is then associated with the idler roller 108 by threading the mesh 200 through one side of the idler roller 108 and under the idler roller 108 so that the mesh 200 extends to the other side of the idler roller 108. The mesh 200 is then threaded over the take-up reel 104 such that the mesh 200 coils around the take-up reel 104. It should be appreciated that rotation of the take-up reel 104 and/or the payout reel 106 will cause the mesh 200 to coiling around the take-up reel 104 and/or the payout reel 106, respectively. Thus, the flow path of the foil mesh 200 is to coil around the payout reel 106, into the tank cavity 120 and under the idler roller 108. The mesh flow path of the mesh 200 then extends out of the tank cavity 120 and coils around the take-up reel 104. As such, if the tank cavity 120 includes a coating solution 122, then as the foil mesh 200 traverses the mesh flow path, then the mesh 200 will be bathed in the coating solution 122 for a period of time. Accordingly, the period of time that the mesh 200 is bathed in the coating solution 122 depends on how fast the mesh 200 is traversing the mesh flow path which can be controlled by controlling the rotational velocity of the take-up reel 104 and/or the payout reel 106.

It should be appreciated that in one embodiment, more than one take-up reel 104, payout reel 106 and/or idler roller 108 may be used. For example, in one embodiment an additional floating bar and/or idler roller 108 may be included proximate the take-up reel and before actual spooling. And in another embodiment, multiple idler rollers 108 (for example, three) may be used upon exit of the mesh 200 from the solution tank 102. This advantageously allows the mesh web to flow easier thereby allowing for a better (tighter and/or straighter) take-up. Additionally, this may also allow for open air drying time after vacuuming. Moreover, it should be appreciated that in one or more embodiments, the payout reel 108 is configured to rotate freely and is not controlled and/or driven. In this embodiment, a slight break may be applied so the mesh roll 200 does not start unspooling itself. Thus, the take-up reel 104 is configured to have enough pulling force to move the mesh roll 200 at a desired speed through the flow path. Additionally, the take-up reel 104 may be controllably adjusted as the weight of the mesh roll 200 increases/decreases.

Moreover, referring to FIG. 4B, in one embodiment a vacuum 132 may be included and configured to be associated with the aluminum and/or copper foil mesh to remove excess solution after bathing. In this embodiment, the mesh roll 200 would be run under the vacuum 132. It should be appreciated that the annealing process which is conducted prior to bathing the mesh roll 200 in the solution tank 102, helps soften and relax the mesh roll 200 to assure an even drag over/under the vacuum bar with full contact between the vacuum bar 132 and the material on the mesh roll 200.

Figure 5:
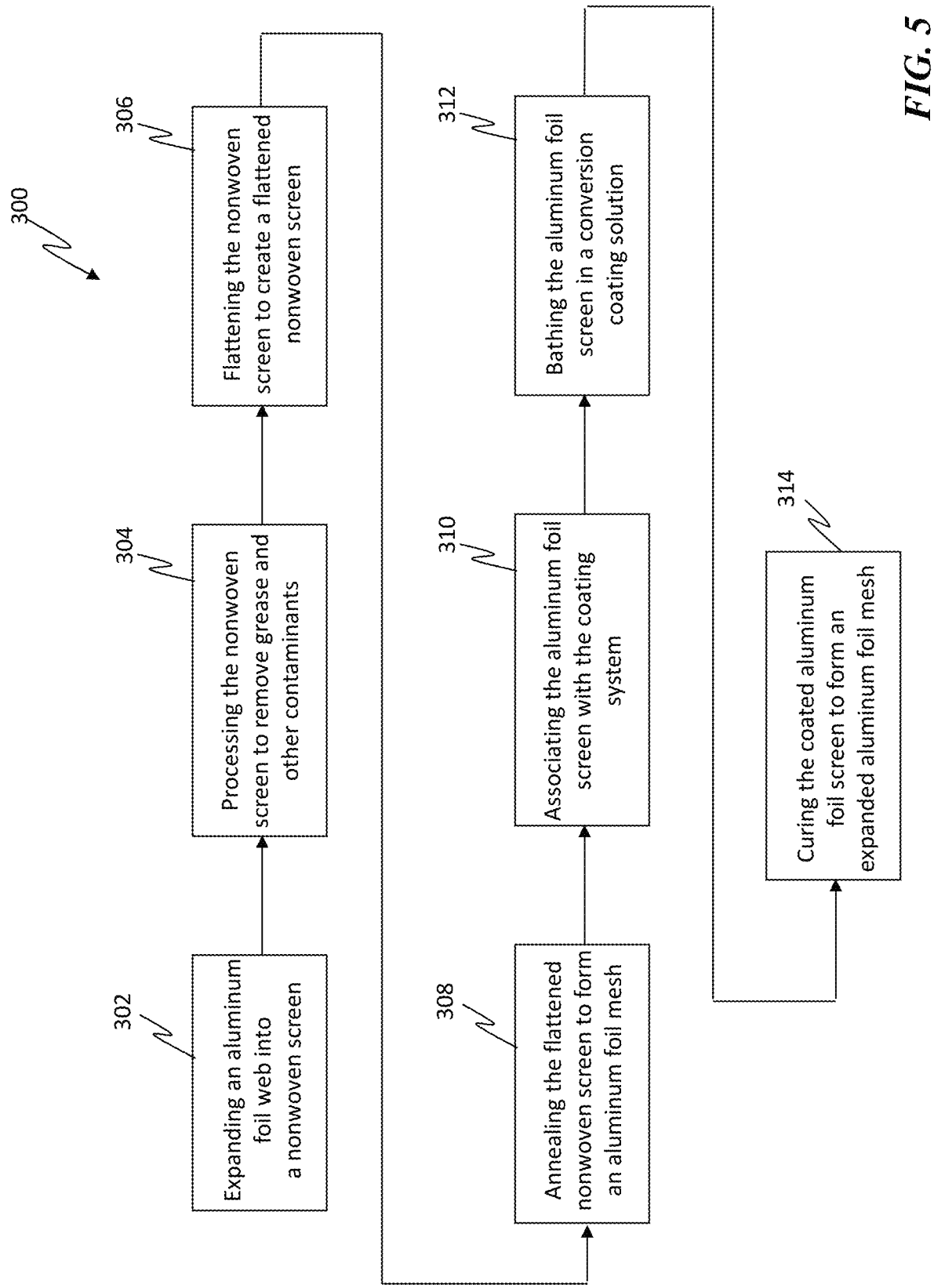
FIG. 5 illustrates an operational block diagram of a method for coating an aluminum foil mesh with a non-chromate conversion coating, accordance with one embodiment of the invention.
Figure 6:
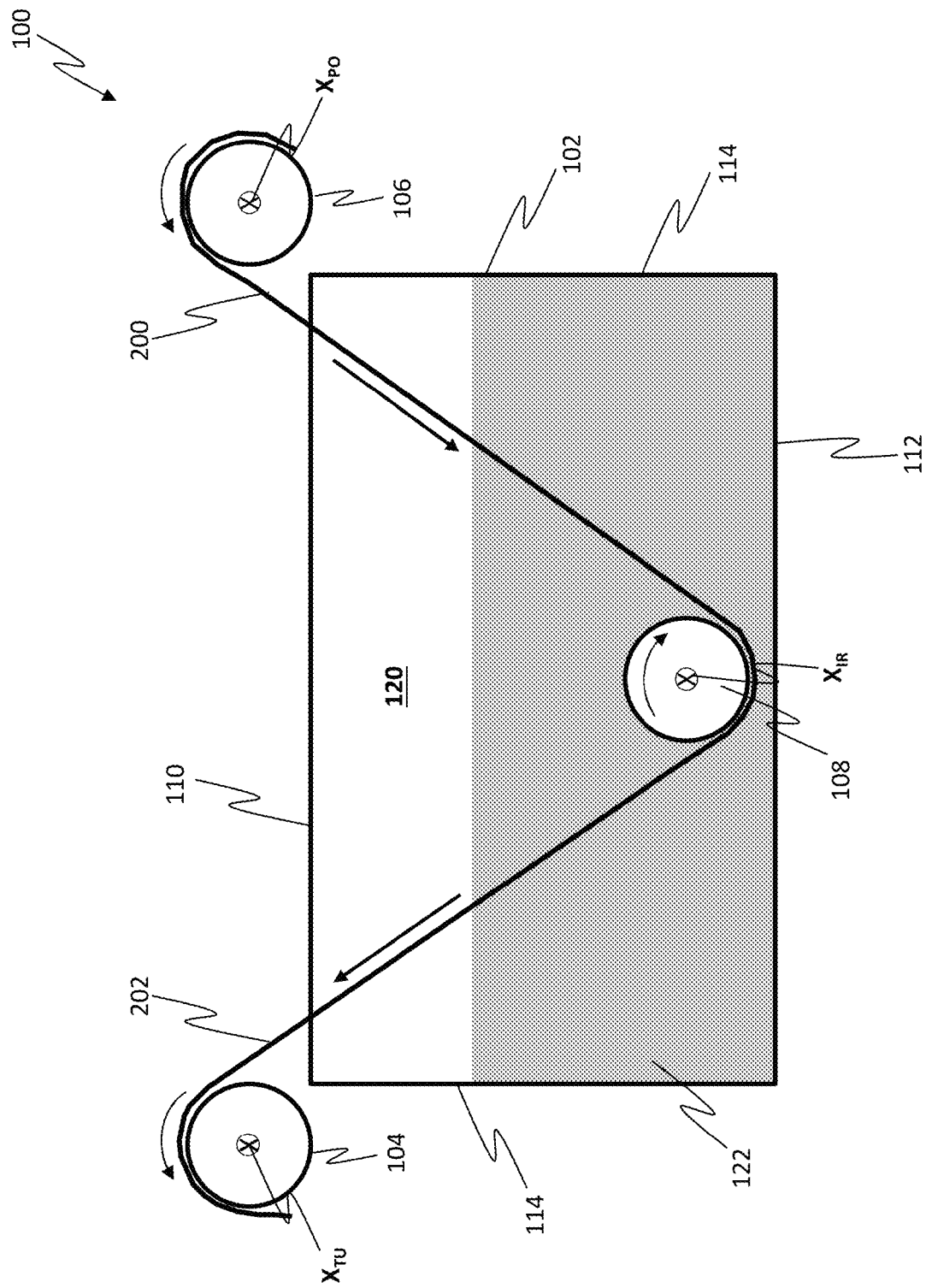
FIG. 6 shows a side sectional view of a solution tank for use in implementing the method of FIG. 5, with an aluminum web installed, in accordance with one embodiment of the invention.

In accordance with one embodiment of the invention and referring to FIG. 5 and FIG. 6, a method 300 for coating an aluminum foil mesh with a non-chromate conversion coating is provided and includes expanding an aluminum foil web (or sheet) into a nonwoven screen, as shown in operational block 302. The method 300 further includes processing the nonwoven screen to remove any grease and/or other surface contaminants, as shown in operational block 304. It should be appreciated that this may be accomplished by exposing the nonwoven screen to various degreasing solvents, such as Bromomethane (methyl bromide). The method 300 further includes creating a flattened nonwoven screen, as shown in operational block 306. This may be accomplished by flattening the nonwoven screen to a thickness range of between approximately 0.002 inches and approximately 0.006 inches. The flattened nonwoven screen is annealed to form an aluminum foil mesh 200, as shown in operational block 308. Although this annealing process is preferably accomplished at a temperature of approximately 600° F. with an approximate 2 (two) -3 (three) hour soak, any annealing method suitable to the desired end purpose may be used, such as that which is well understood by those skilled in the art. It should be appreciated that this softens and relaxes the aluminum foil mesh 200 to assure an even drag over the vacuum bar 132 with full contact between the screen and the vacuum bar during the excess solution removal operation.

The method 300 further includes associating the aluminum foil mesh 200 with the coating system 100, as shown in operational block 310. It should be appreciated that this may be accomplished by associating the aluminum foil mesh 200 with the payout reel 106 such that the aluminum foil mesh 200 coils around the payout reel 106 and traverses the mesh flow path as previously described hereinabove. Thus, as the aluminum foil mesh 200 traverses the mesh flow path, the aluminum foil mesh 200 is located under the idle roller 108 and further associated with the take-up reel 104 such that the aluminum foil mesh 200 coils around the take-up reel 104. Accordingly, as the take-up reel 104 and/or payout reel 106 rotate about the take-up reel axis $X_{TU}$ and/or the payout reel axis $X_{PO}$ friction between the aluminum foil mesh 200 and take-up reel 104 and/or payout reel 106 causes the aluminum foil mesh 200 to traverse the mesh flow path as previously described hereinabove.

The method 300 further includes controllably bathing the aluminum foil mesh 200 in a conversion coating solution 122 via the coating system 100 to create a coated aluminum foil mesh 202, as shown in operational block 312. This may be accomplished by putting a conversion coating solution 122 comprised of approximately 5% butyl benzotriazole sodium salt within the tank cavity 120 and maintaining the conversion coating solution 122 at a temperature of approximately 78° F. It should be appreciated that the amount of conversion coating solution 122 contained with the tank cavity 120 should be sufficient to fill the tank cavity to a predetermined level as the aluminum foil mesh 200 traverses the mesh flow path, the aluminum foil mesh 200 is located within the conversion coating solution 122 for a period of approximately 30 seconds. In one embodiment, the method 300 may further include removing excess solution from the coated aluminum foil mesh 202. This may be accomplished by vacuuming (or other removing process as desired) the excess solution from the coated aluminum foil mesh 202 using a vacuum. One type of vacuum may be a vacuum bar which has a ⅛ inch×37 inch suction slot and is rated for 407 CFM. The removed excess solution may be stored in a tank and discarded (or filtered and reused). Moreover, the method 300 includes curing the coated aluminum foil mesh 202 to form an expanded aluminum foil mesh, as shown in operational block 314. This may be accomplished by locating the coated aluminum foil mesh 202 within a low moisture environment for approximately 18 hours.

Figure 7:
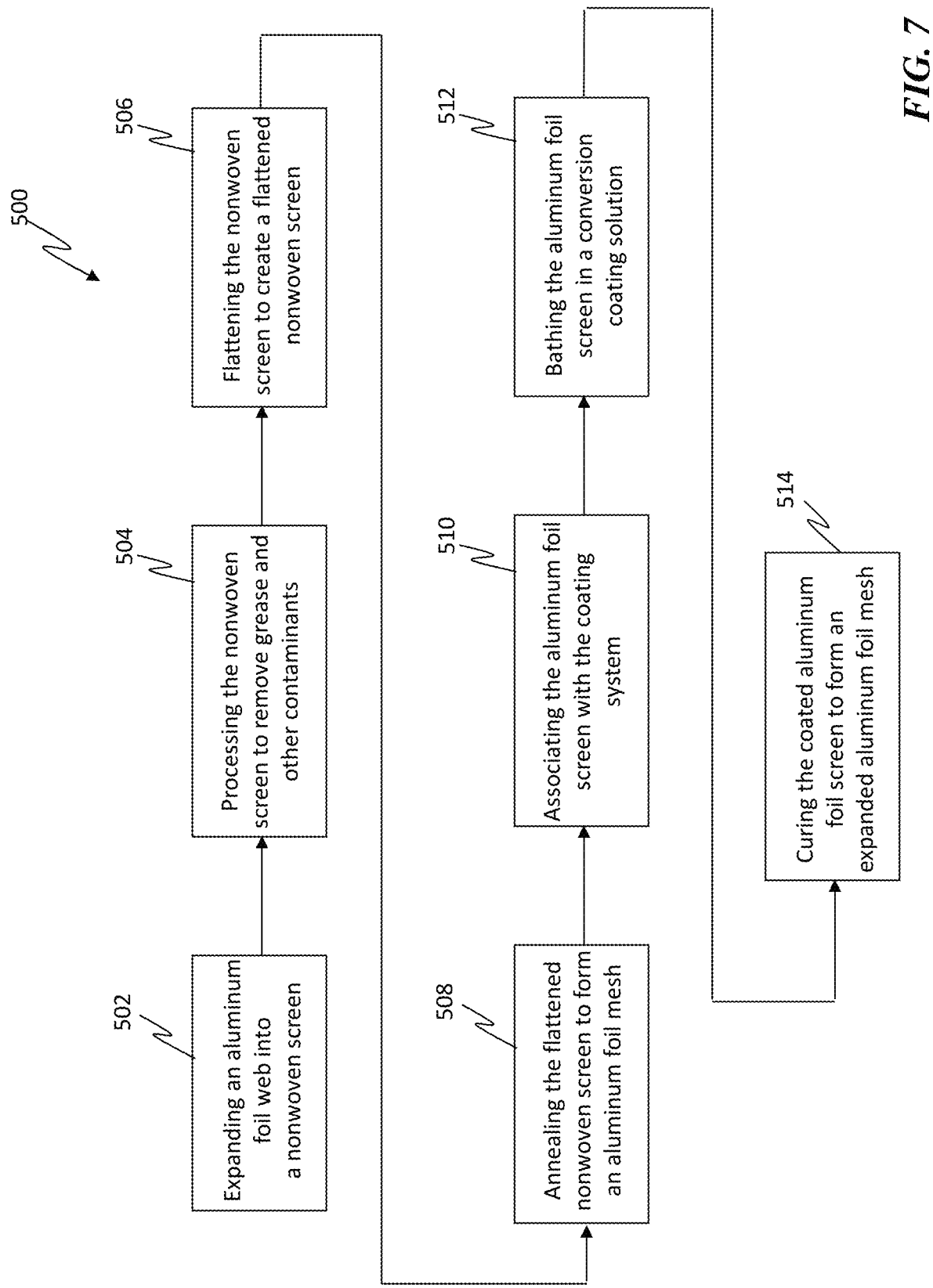
FIG. 7 illustrates an operational block diagram of a method for coating a copper foil mesh with a non-chromate conversion coating, accordance with one embodiment of the invention.
Figure 8:
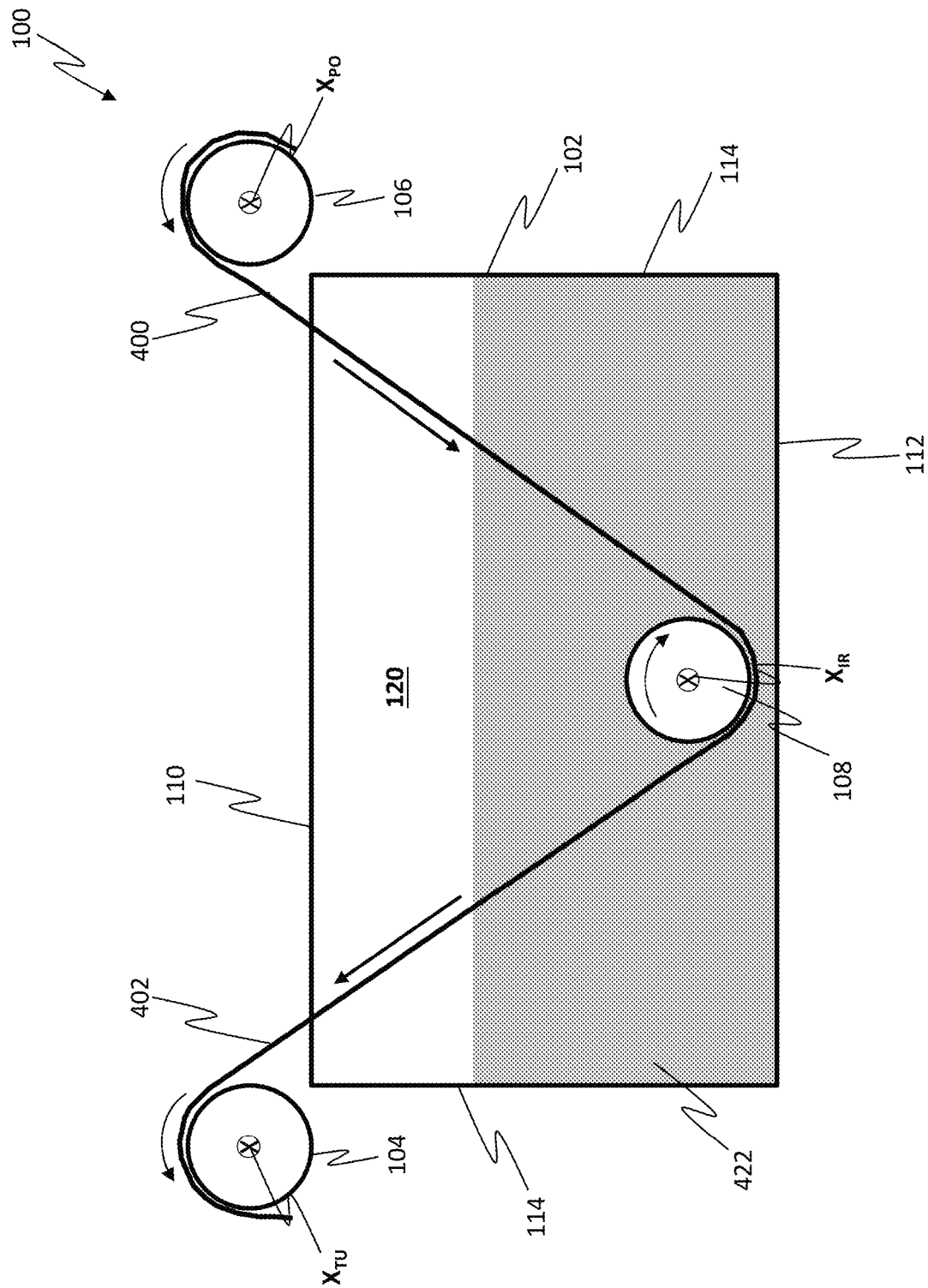
FIG. 8 shows a side sectional view of a solution tank for use in implementing the method of FIG. 7, with a copper web installed, in accordance with one embodiment of the invention.

In accordance with one embodiment of the invention and referring to FIG. 7 and FIG. 8, a method 500 for coating a copper foil mesh with a non-chromate conversion coating is provided and includes expanding an copper foil web (or sheet) into a nonwoven screen, as shown in operational block 502. The method 500 further includes processing the nonwoven screen to remove any grease and/or other surface contaminants, as shown in operational block 504. It should be appreciated that this may be accomplished by exposing the nonwoven screen to various degreasing solvents, such as Bromomethane (methyl bromide). The method 500 further includes creating a flattened nonwoven screen, as shown in operational block 506. This may be accomplished by flattening the nonwoven screen to a thickness range of between approximately 0.002 inches and approximately 0.006 inches. The flattened nonwoven screen is annealed to form a copper foil mesh 400, as shown in operational block 508. Although this annealing process is preferably accomplished at a temperature of approximately 600° F. with an approximate 3 (three) hour soak, any annealing method suitable to the desired end purpose may be used, such as that which is well understood by those skilled in the art.

The method 500 further includes associating the aluminum foil mesh 400 with the coating system 100, as shown in operational block 510. It should be appreciated that this may be accomplished by associating the copper foil mesh 400 with the payout reel 106 such that the copper foil mesh 400 coils around the payout reel 106 and traverses the mesh flow path as previously described hereinabove. Thus, as the copper foil mesh 400 traverses the mesh flow path, the copper foil mesh 400 is located under the idle roller 108 and further associated with the take-up reel 104 such that the copper foil mesh 300 coils around the take-up reel 104. Accordingly, as the take-up reel 104 and/or payout reel 106 rotate about the take-up reel axis $X_{TU}$ and/or the payout reel axis $X_{PO}$, friction between the copper foil mesh 400 and take-up reel 104 and/or payout reel 106 causes the copper foil mesh 400 to traverse the mesh flow path as previously described hereinabove.

The method 500 further includes controllably bathing the copper foil mesh 400 in a conversion coating solution 422 via the coating system 100 to create a coated copper foil mesh 402, as shown in operational block 512. This may be accomplished by putting a conversion coating solution 422 comprised of a 7% alodine 5200 solution within the tank cavity 120 and maintaining the conversion coating solution 422 at a temperature of approximately 78° F. It should be appreciated that the amount of conversion coating solution 422 contained with the tank cavity 120 should be sufficient to fill the tank cavity to a predetermined level as the copper foil mesh 400 traverses the mesh flow path, the copper foil mesh 400 is located within the conversion coating solution 422 for a period of approximately 30 seconds. In one embodiment, the method 500 may further include removing excess solution from the coated aluminum foil mesh 402. This may be accomplished by vacuuming (or other removing process as desired) the excess solution from the coated aluminum foil mesh 402 using a vacuum. One type of vacuum may be a vacuum bar which has a ⅛ inch×37 inch suction slot and is rated for 407 CFM. The removed excess solution may be stored in a tank and discarded (or filtered and reused). Moreover, the method 500 includes curing the coated copper foil mesh 402 to form an expanded copper foil mesh, as shown in operational block 514. This may be accomplished by locating the coated copper foil mesh 402 within a low moisture environment for approximately 18 hours.

It should be appreciated that the rotational velocity of the take-up reel 104 and/or payout reel 106 may be controlled to control the amount of time it takes the aluminum foil mesh 200/202 and/or the copper foil mesh 400/402 to traverse the mesh flow path. This allows the system 100 to control the amount of time the aluminum foil mesh 200/202 and/or the copper foil mesh 400/402 is contained with the conversion coating solution 122/422. If less time is required in the conversion coating solution 122/422, the velocity of the take-up reel 104 and/or payout reel 106 is increased. If more time is required in the conversion coating solution 122/422, the velocity of the take-up reel 104 and/or payout reel 106 is decreased.

It should be appreciated that the coating solution 122/422 may be maintained to remove impurities as desired. For example, in one embodiment the coating solution 122/422 may be analyzed to determine whether the coating solution 122/422 is too "dirty." If the coating solution 122/422 is determined to have too many impurities, the coating solution 122/422 may be changed or filtered as desired. Additionally, the coating solution 122/422 may be analyzed to determine the Parts Per Million (PPM) of one or more specific chemicals that make up the coating solution 122/422. For example, if the parameters of the coating solution 122/422 require the coating solution to have a solution PPM of 150 PPM+/−20 PPM, and the solution PPM is too high, then a diluting agent (such as water) may be added to the coating solution 122/422 to bring the solution PPM to be within the 150 PPM+/−20 PPM parameter. If the solution PPM is too low, then more chemical may be added to the coating solution 122/422 to bring the solution PPM to be within the 150 PPM+/−20 PPM parameter.

Additionally, it should be appreciated that as the excess coating solution 122/422 is vacuumed off of the foil mesh 202/402, the level of the coating solution 122/422 within the tank cavity 120 becomes depleted. After a predetermined amount of coating solution 122/422 is depleted from the tank cavity 120 (for example, when the level of the coating solution 122/422 within the tank cavity 120 depletes by 1 inch) new coating solution 122/422 may be added to the tank cavity 120 to bring the level of the coating solution 122/422 within the tank cavity 120 to a desired level. It should be appreciated that the coating solution 122/422 within the tank cavity 120 may be replaced after being exposed to a predetermined amount of material 200/400 as desired. For example, in one embodiment after 15,000 square feet of mesh material 200/400 has run through the coating solution 122/422, the tank cavity 120 may be drained and refilled with a fresh mixture of coating solution 122/422.

In accordance with the present invention, the method 200, 500 of the invention may be implemented, wholly or partially, by a controller operating in response to a machine-readable computer program. In order to perform the prescribed functions and desired processing, as well as the computations therefore (e.g. execution control algorithm(s), the control processes prescribed herein, and the like), the controller may include, but not be limited to, a processor(s), computer(s), memory, storage, register(s), timing, interrupt(s), communication interface(s), and input/output signal interface(s), as well as combination comprising at least one of the foregoing.

Moreover, the method 200, 500 of the present invention may be embodied in the form of a computer or controller implemented processes. The method 200, 500 of the invention may also be embodied in the form of computer program code containing instructions embodied in tangible media, such as floppy diskettes, CD-ROMs, hard drives, Solid State Drives (SSD) and/or any other computer-readable medium, wherein when the computer program code is loaded into and executed by a computer or controller, the computer or controller becomes an apparatus for practicing the invention. The invention can also be embodied in the form of computer program code, for example, whether stored in a storage medium, loaded into and/or executed by a computer or controller, or transmitted over some transmission medium, such as over electrical wiring or cabling, through fiber optics, or via electromagnetic radiation, wherein when the computer program code is loaded into and executed by a computer or a controller, the computer or controller becomes an apparatus for practicing the invention. When implemented on a general-purpose microprocessor the computer program code segments may configure the microprocessor to create specific logic circuits.

It should be appreciated that while the invention has been described with reference to an exemplary embodiment, it will be understood by those skilled in the art that various changes, omissions and/or additions may be made and equivalents may be substituted for elements thereof without departing from the spirit and scope of the invention. In addition, many modifications may be made to adapt a particular situation or material to the teachings of the invention without departing from the scope thereof. Moreover, it is contemplated that elements of one embodiment may be combined with elements of other embodiments as desired. Therefore, it is intended that the invention not be limited to a particular embodiment disclosed herein as the best mode contemplated for carrying out this invention, but that the invention will include all embodiments (individually and/or combined) falling within the scope of the appended claims and/or information. Moreover, unless specifically stated any use of the terms first, second, etc. do not denote any order or importance, but rather the terms first, second, etc. are used to distinguish one element from another.

We claim:

1. A system for coating a foil mesh with a no-chrome conversion coating, the system comprising:
   a solution tank, wherein the solution tank includes a tank first end and a tank second end and defines a tank cavity for containing a conversion coating solution, wherein the conversion coating solution comprises at least one of 5% butyl benzotriazole sodium salt and 7% alodine 5200;
   at least one reel configured to cause the foil mesh to traverse the solution tank; and
   at least one roller, wherein the at least one of the at least one reel and the at least one roller is configured to immerse the foil mesh within the conversion coating solution when a conversion coating solution is located within the tank cavity.

2. The system of claim 1,
   wherein the at least one reel includes a payout reel and a take-up reel, wherein the payout reel is located proximate the tank first end and the take-up reel is located proximate the tank second end, and
   wherein the at least one roller includes an idler roller, wherein the idler roller is located within the tank cavity and disposed such that when a conversion coating solution is located within the tank cavity, the idler roller is at least partially immersed within the conversion coating solution.

3. The system of claim 2, further comprising a first control device associated with the take-up reel and configured to controllably cause the take-up reel to rotate about the take-up reel axis.

4. The system of claim 2, further comprising a second control device associated with the payout reel and configured to controllably cause the payout reel to rotate about the payout reel axis.

5. The system of claim 2, wherein the idler roller includes an idler roller axis and is configured to rotate about the idler roller axis.

6. The system of claim 2, wherein the take-up roller includes a take-up roller surface which is configured to frictionally engage with the foil mesh.

7. The system of claim 2, wherein the payout roller includes a payout roller surface which is configured to frictionally engage with the foil mesh.

8. The system of claim 2, wherein the foil mesh is at least one of aluminum and copper.

9. A system for coating a foil mesh with a no-chrome conversion coating, the system comprising:
   a solution tank, wherein the solution tank defines a tank cavity for containing a conversion coating solution, wherein the conversion coating solution comprises at least one of 5% butyl benzotriazole sodium salt and 7% alodine 5200;
   a reel/roller system configured to cause the foil mesh to be disposed within the conversion coating solution for a predetermine period of time.

10. The system of claim 9, wherein the reel/roller system includes,
    a payout reel, wherein the payout reel is located proximate a first solution tank end;
    a take-up reel, wherein the take-up reel is located proximate a second solution tank end; and
    a roller, wherein the roller is located within the tank cavity and configured to cause the foil mesh to be bathed within the conversion coating solution.

11. The system of claim 10, wherein the payout reel includes a payout reel axis and is configured to rotate about the payout reel axis.

12. The system of claim 11, wherein the take-up reel includes a take-up reel axis and is configured to rotate about the take-up reel axis.

13. The system of claim 12, further comprising a first control device associated with the take-up reel and configured to controllably cause the take-up reel to rotate about the take-up reel axis.

14. The system of claim 11, further comprising a second control device associated with the payout reel and configured to controllably cause the payout reel to rotate about the payout reel axis.

15. The system of claim 10, wherein the idler roller includes an idler roller axis and is configured to rotate about the idler roller axis.

16. The system of claim 10, wherein the payout reel, the take-up reel and the roller are configured to cause the foil mesh to traverse the tank cavity such that the foil mesh is located within the conversion coating solution for a predetermine period of time.

17. A method for coating a foil mesh with a non-chromate conversion coating, the method comprising:
    expanding a foil web into a nonwoven screen;
    processing the nonwoven screen to create a foil mesh;
    bathing the foil mesh within a conversion coating solution comprising at least one of 5% butyl benzotriazole sodium salt and 7% Alodine 5200 for a predetermined amount of time to create a coated foil mesh; and
    curing the coating foil mesh for approximately 18 hours to create an expanded foil mesh.

18. The method of claim 17, wherein processing includes,
    treating the nonwoven screen to remove grease and other surface contaminants;
    flattening the nonwoven screen to a thickness of between about 0.002 inches and about 0.006 inches to create a flattened nonwoven screen, and
    annealing the flattened nonwoven screen to create the foil mesh.

19. The method of claim 17,
    wherein the foil mesh is constructed from at least of aluminum and copper, and
    wherein the conversion coating solution is a solution comprising at least one of 5% butyl benzotriazole sodium salt and 7% alodine 5200.

20. The method of claim 17, wherein the predetermine amount of time is approximately 30 seconds±5 seconds.

* * * * *